United States Patent

Preussner

[11] Patent Number: 6,056,402
[45] Date of Patent: May 2, 2000

[54] PHOROMETER OPERATED BY AN ELECTRIC MOTOR

[76] Inventor: Paul Rolf Preussner, Am Linsehberg 18, D-55131 Mainz, Germany

[21] Appl. No.: 09/180,505
[22] PCT Filed: May 13, 1997
[86] PCT No.: PCT/DE97/00989
  § 371 Date: Nov. 12, 1998
  § 102(e) Date: Nov. 12, 1998
[87] PCT Pub. No.: WO97/43945
  PCT Pub. Date: Nov. 27, 1997
[51] Int. Cl.⁷ .......................................................... A61B 3/10
[52] U.S. Cl. ............................................................... 351/216
[58] Field of Search ................................... 351/200, 222, 351/216, 217, 218, 246; 359/666

[56] References Cited

U.S. PATENT DOCUMENTS 5,739,959  4/1998  Quaglia ..................................... 359/666
5,914,772  6/1999  Dyer ........................................ 351/246

*Primary Examiner*—George Manuel

[57] ABSTRACT

An electromotive driven phoropter is described. In this phoropter the rotating components (revolving discs for spherical lenses, as well as Stokes' lenses for the cylinder glasses) are driven by a special, electromagnetic, friction- and slip-free direct drive.

On each rotor are fitted yokes made of magnetisable material at adequate angle distances and opposite them, on the respective stator, electromagnets also at equidistant angle distances which, however, differ from those of the yokes. Yokes and electromagnets fulfil a "vernier condition" with respect to their angle distances. Therefor the smallest setting angle is given by the difference in the angle distances of the yokes and electromagnets.

8 Claims, No Drawings

PHOROMETER OPERATED BY AN ELECTRIC MOTOR

TECHNICAL FIELD

The invention is an optomechanical device for the ophthalmologist or optician with which the test glasses can be varied in the course of the subjective adjustment of correction glasses.

STATE OF TECHNOLOGY

In the course of the subjective adjustment of correction glasses (spectacles or contact lenses) in general nowadays what is known as a "phoropter" is used for presenting the test glasses. In this connection, in state-of-the-art devices (e.g. U.S. Pat. No. 4,500,180, DE2901459) spherical and cylindrical lenses for each eye are usually arranged on lens discs (revolving wheels). Other versions (e.g. DE3331799) use a pair of Stokes' lenses, as they have been known since the mid-nineteenth century, as cylinder glasses. The mechanical construction with these Stokes' lenses is considerably simpler as only two lenses all told are required for all cylinder strengths and axes, however, rather high demands are made on the setting accuracy for the rotation of both lenses against one another and the link between the relative angle and the resultant cylinder strength is not linear. A pair of Stokes' lenses can therefore only be implemented in practice in a phoropter together with a computer which calculates the relative angle required in each step for the cylinder strength desired and which controls an electric motor drive for each lens ensuring an adequate setting accuracy.

In general, stepper motors meeting state-of-the-art requirements are usually used nowadays for phoropter drives, either for the revolving wheels with or without planetary gears, or for Stokes' lenses. These stepper motors then drive the mountings of the optical components through appropriate mechanical gear reductions meaning in most cases not inconsiderable complexity with corresponding possible faults and production costs. In addition, the mechanical dimensions of such phoropters are quite large. Recently, phoropters have also become available on the market (DE4425443) which, instead of the stepper motor drives mentioned, use electrostrictive (in general piezoelectric) stepper micromotors. With these drives, the mechanical complexity is markedly less and the positioning accuracy (number of steps per rotation) is greater too. Admittedly, these drives usually display a certain amount of "slippage" so that additional means have to be taken for the continuous position measurement. As well as that, very tight production tolerances must be met which additionally increases the costs.

The task of this present invention is to make available a phoropter with an electromechanical drive which combines a very high setting accuracy with very small mechanical dimensions and little production complexity.

SHORT DESCRIPTION OF THE INVENTION

The task is solved in the invention in accordance with the characteristic features of claim 1.

In order to move the rotating components (revolving wheels or Stokes' lenses, hereinafter called "rotors" while the stationary parts of the drive are called "stators" as a whole) an electromagnetic direct drive is used, as is known in another connection, for example from U.S. Pat. No. 4,596,449, which is implemented in the following manner.

On a circumference periphery of each rotor n magnetisable components of the same kind (hereinafter called "yokes") are located at constant angle distances $\alpha$, fastened in non-magnetisable surroundings. Directly opposite the same on a circumference periphery of the stator are located m electromagnets of the same kind also at constant angle distances $\beta$. The centre-points of the two said circumferences lie on the axis of rotation and the rest of the geometry is arranged in such a manner that the electromagnets and yokes stand opposite to each other separated only by a small air gap. The angle distances $\alpha$ and $\beta$ are chosen in such a manner that a "vernier arrangement" results for the positions of the yokes and electromagnets with respect to one another, that means that for the differential angle $\gamma=|\alpha-\beta|$ either $m\cdot\gamma=\alpha$ and $(m+1)\cdot\gamma=\beta$ or $n\cdot\gamma=\beta$ and $(n+1)\cdot\gamma=\alpha$ is fulfilled. If a yoke now stands exactly opposite an electromagnet as the starting position, the rotor can be moved on by the angle $\gamma$ by switching on the neighbouring electromagnet to the said one. If $\alpha$ and $\beta$ differ only a little from one another, very small adjustment angles $\gamma$ can be achieved reproducibly as well as slipfree and friction-free, without the need for any kind of mechanical gear reduction.

PREFERRED VERSION AND ALTERNATIVE VERSIONS

The phoropter in its usual construction consists of two sub-units of the same kind at a distance from one another which can be adjusted in accordance with the spacing of the eyes of the person to be examined. In each of these sub-units there are several revolving discs for the spherical glasses and for the accessory glasses (polarisation filters, apertures, shutter, etc.) in known technology. The said revolving discs rotate round a common axis. In the optical axis of the eye to be refracted there are in addition a pair of Stokes' lenses for the cylinder glasses.

In another version of the invention one planetary gear each in known technology can also be employed for the revolving wheels for the cylinder glasses and for the common adjustment of the cylinder axes of a revolving wheel, however, in this case the advantages of the invention (less mechanical complexity) are shown less to their advantage.

As an option, the phoropter can also be equipped additionally with a pair of prism compensators in state-of-the-art technology.

As the revolving discs are normally intended to execute complete rotations and must carry lenses or other optical elements in k positions. The number of yokes on them must be divisible by k.

A revolving disc with six positions could thus, for example, be fitted with 30 yokes at an angle distance of $\alpha=12°$. In order to drive it, three electromagnets at an angle distance of $\beta=16°$ are sufficient so that the aforementioned "vernier condition" is fulfilled. Alternating actuation of the electromagnets in the sequence 1-2-3-1-2-3 ... then leads to a continuous rotation which is continued for so long until the desired new position is reached.

In order to rotate the individual lenses of a pair of Stokes' lenses in such a manner that the graduation steps for the said purpose can be implemented in the resultant cylinder strength (normally 0.25 dpt) with sufficient accuracy (better than 0.1 dpt) with a simultaneous setting range of 6.0 dpt in the resultant cylinder strength, the adjustment angle for the individual lens must be $\gamma \leq 1°$. This is achieved, for example, if 25 yokes are mounted on the rotor (Stokes' lens) at a distance of $\alpha=14.4°$ and 16 electromagnets on the appurtenant stator at a distance of $\beta=15.3°$. The adjusting angle is then $\gamma=0.9°$.

The actuation of the electromagnets is made preferably via a computer in such a manner that in one computer word one bit for an electromagnet is set in each case when the said magnet is to be switched on. Then, for example. semiconductor switches can switch a constant current source to the respective magnets via appropriate computer ports. As only one electromagnet is active for a drive at any one moment, the number of lines between the computer and phoropter can be greatly reduced by state-of-the-art electronic multiplexer and demultiplexer modules.

The yokes and electromagnets must be designed in accordance with the known rules of technology in such a manner with respect to their geometry, their material, the air gap between them, as well as the current flowing through the electromagnet that an electromagnet, when actuated electrically, exercises a force on the yoke lying closest to it, i.e. on a yoke that is at an angle distance of $\alpha/2$ at the most to it, which can rotate the rotor, i.e. overcomes at least its bearing friction.

The electromagnet is implemented preferably as two coils arranged alongside one another which are linked mechanically and magnetically to one another by a further yoke on the side facing away from the rotor, because in this manner a low structural height is achieved simultaneously with a high total number of windings for the coils.

With the given "vernier principle", in the case of the required sequence of actuating the electromagnets, the position of the rotor is only unique if the starting position is definite. Otherwise, the (stable) rotor position is n-times ambiguous for an actuated electromagnet.

For these reasons, position measuring devices must be provided in order to achieve a defined starting position. Forked or reflecting light barriers in state-of-the-art versions can, for example, be used for this purpose. Their angle resolution may be markedly poorer than the positioning accuracy $\gamma$ achievable with the "vernier drive".

Theoretically, a resolution better than $\alpha/2$ is sufficient with which a marking on a periphery of the rotor must be recognised. With an unknown rotor position, a start or reset procedure will then be implemented in the following manner. Firstly, the electromagnets will be actuated cyclically one after the other. At each step, the position measuring device is interrogated whether it has recognised the mark. If this is the case, then only an electromagnet designated as "No. 1" will be switched on so that the rotor will only rotate by the angle which magnet No. 1 is distant from the nearest yoke. When both stand above one another, the desired starting position has been reached. Starting out from this starting position, each new position is uniquely settable just by the switching a sequence of the electromagnets. A new reset procedure is thus only required after switching power off and on again, or after the occurrence of a fault.

With respect to the arrangement of electromagnets and yokes, in particular also with respect to the orientation of the magnetic field between them (parallel or vertical, or also at other angles to the rotor axis), numerous variants are possible, depending mainly on the desired casing shape or production technology aspects.

A particularly simple and advantageous construction from a production technology aspect results when the electromagnets for one or even for two adjoining rotors are fitted on an electronic pc board on which their actuating electronics (semiconductor switches, possibly demultiplexer) is also mounted.

To operate the phoropter, the set value requirements for the glasses should be made either by a manual-electronic operating unit or by an automatic refraction device, such as is known from DE4124056 or by a combination of both permitting manual or automatic refracting alternatively. For this purpose, state-of-the-art electronic interfaces must then be provided.

When operating with a manual-electronic operating unit, such values for the cylinder strength or axis as are implemented with the help of cross-cylinder glasses in manual phoropters, can then also be calculated and set, as is known, for example from DE2901459, using electronic means.

If the numbers of the yokes n and electromagnets m are not relatively prime, then drives in accordance with the invention are constructable in which the afore-mentioned vernier condition refers to integral fractions of n and/or m.

What is claimed is:

1. Electromotive driven phoropter with
    at least one rotatable optical element (rotor) through the rotation of which the optical effect is changed,
    an electromotive drive to rotate the optical element,
    an electronic control device for the manual or program-controlled setting of the respective optical effect,
characterised by the fact that the electromotive drive is implemented as a direct drive in the sense of a stepper motor as follows:
    n magnetisable, structurally identical yokes are fastened on the rotor on a circumference periphery at constant angle distances $\alpha$ in non-magnetisable surroundings whereby the circle normal line is the rotating axis of the rotor;
    m structurally identical electromagnets are fastened on a stationary stator located opposite the rotor at constant angle distances $\beta$ in non-magnetisable surroundings on a circumference periphery whereby the circle normal line is the rotating axis of the rotor;
    the arrangement is made in such a manner that one actuated electromagnet in each case attracts a yoke that is less than $\alpha/2$ distant from it, thus driving the rotor;
    the angles $\alpha$ and $\beta$ are selected in such a manner that they fulfill a "vernier condition", that means for angle $\gamma=|\alpha-\beta|$ either $m\cdot\gamma=\alpha$ and $(m+1)\cdot\gamma=\beta$ or $n\cdot\gamma=\beta$ and $(n+1)\cdot\gamma=\alpha$ apply, whereby n and m are relatively prime, or a corresponding condition applies for an integral fraction of n and/or m;
    an electronic switching device activates the electromagnets in such a manner that the optical element moves in accordance with the settings of the control device.

2. Phoropter in accordance with claim 1, characterised by the fact that a position measuring device, for example a light barrier, is provided for the rotor, which recognises at least one position of the rotor with an angle resolution of at least $\alpha/2$.

3. Phoropter in accordance with claim 1, characterised by the fact that revolving discs are fitted as optical elements for the incorporation of lenses or other optical components, whereby by rotating the revolving disc another component is moved into the optical axis in each case.

4. Phoropter in accordance with claim 1, characterised by the fact that Stokes' lenses are present in the optical axis as optical elements and are rotatable around the same.

5. Phoropter in accordance with claim 4, characterised by the fact that so a manual-electronic operating unit is provided with which the operator can change the cylinder strength or cylinder axis of supplementary lenses in apparently the same manner for him as by the known cross cylinder, whereby, however, in fact electronic means are provided which calculate this change in the supplementary glasses by superimposition of this apparent cross cylinder and actuate the Stokes' lenses accordingly.

6. Phoropter in accordance with claim 1, characterised by the fact that prisms are present in the optical axis as optical elements and are rotatable around the same.

7. Phoropter in accordance with claim 1, characterised by the fact that the electromagnets for one rotor or for two adjoining rotors are mounted together with their actuating electronics on a module (pc board).

8. Phoropter in accordance with claim 1, characterised by the fact that an electronic interface is provided via which the set values for the phoropter settings are given by a manual-electronic operating unit and/or by an automatic refracting device.

* * * * *